(12) United States Patent
Stobart

(10) Patent No.: US 6,554,168 B2
(45) Date of Patent: Apr. 29, 2003

(54) GLOVE REMOVAL AND/OR RETENTION

(76) Inventor: Allan William Stobart, Low Currigg, Raughton Head, Dalston, Carlisle, Cumbria, C45 7DX (GB)

( * ) Notice: Subject to any disclaimer, the term of this patent is extended or adjusted under 35 U.S.C. 154(b) by 22 days.

(21) Appl. No.: 09/755,275

(22) Filed: Jan. 5, 2001

(65) Prior Publication Data

US 2001/0007329 A1 Jul. 12, 2001

(30) Foreign Application Priority Data

Jan. 8, 2000 (GB) .............................................. 0000335

(51) Int. Cl.$^7$ .............................................. A47G 25/90
(52) U.S. Cl. ...................................................... 223/111
(58) Field of Search ................................ 223/111, 120, 223/1, 112; 138/92

(56) References Cited

U.S. PATENT DOCUMENTS

| | | | |
|---|---|---|---|
| 3,410,522 A | * | 11/1968 | Daghe et al. |
| 3,550,637 A | * | 12/1970 | Bridon |
| 3,695,493 A | * | 10/1972 | Karr .............................. 223/111 |
| 4,002,276 A | * | 1/1977 | Poncy et al. ................. 223/111 |
| 4,228,935 A | | 10/1980 | Madray ......................... 223/111 |
| 4,898,309 A | | 2/1990 | Fischer .......................... 223/111 |
| 4,914,258 A | * | 4/1990 | Jackson |
| 4,915,272 A | | 4/1990 | Volck ............................ 223/111 |
| 5,078,308 A | * | 1/1992 | Sullivan ........................ 223/111 |
| 5,868,290 A | * | 2/1999 | Green, Sr. et al. ........... 223/111 |

* cited by examiner

*Primary Examiner*—Bibhu Mohanty
(74) *Attorney, Agent, or Firm*—Drinker Biddle & Reath LLP

(57) ABSTRACT

The present invention provides glove removal and/or retention apparatus and a method of removing and putting on gloves using the apparatus.

Figure 1:
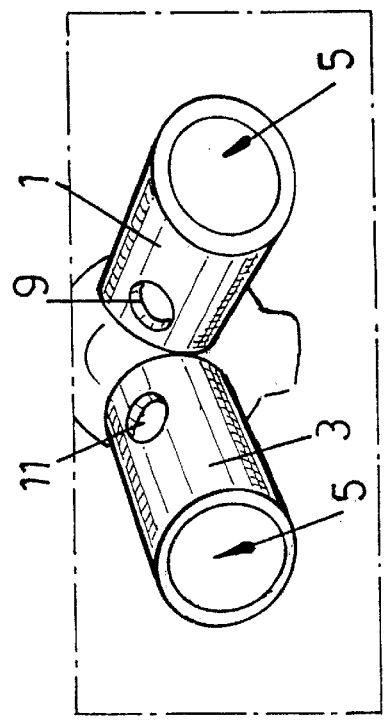

The apparatus comprises housing means having a respective opening to receive, in use, a respective left and right gloved hand. The housing means comprises a hollow tube whose interior is contactable with the exterior of each glove in a light gripping or frictional manner which offers a resistance to removal of the glove on withdrawal of a hand from the glove. The housing provides abutment means for limiting the distance that the glove can be inserted into the housing. The abutment means is positioned to contact the gloved hand between the thumb and index finger and in a preferred embodiment consists apertures into which a thumb of each gloved hand is inserted. The apertures are positioned so that the gloved thumb of one hand can be contacted by the gloved thumb of the other hand. The housings retain the gloves so that the operator can put them on or take them off without having to contact the exterior of the gloves with his bare hands. The apparatus is particularly suited to the removal of relatively loose fitting industrial rubber gloves.

8 Claims, 1 Drawing Sheet

GLOVE REMOVAL AND/OR RETENTION

The present invention relates to glove removal and/or retention.

There are many situations which call for the wearing of gloves to protect a person's hands from coming into contact with hazardous substances. Health and safety requirements are becoming increasingly concerned with ensuring that operators put on and remove gloves without contacting the outer contaminated part of the gloves with their exposed skin. This can be quite difficult to achieve. Normally removal dictates several attempts at releasing each glove a little bit at a time by gripping one glove between the thumb and fingers of the other glove to hand to commence release, and then performing a similar operation on the other glove before the thumb and finger are completely released from the first glove. The process can be quite time consuming and the operator then has to store the gloves until required again. Putting on the gloves without contacting the external surface can also cause difficulties.

The present invention aims to solve the above mentioned problems.

Accordingly, a first aspect of the present invention provides apparatus comprising housing means having an opening to receive, in use, a respective left and right gloved hand, the housing means providing means which is contactable with the exterior of each glove in a light gripping or frictional manner which offers a resistance to removal of the glove on withdrawal of a hand from the glove.

More preferably the housing provides abutment means for limiting the distance that the glove can be inserted into the housing. This is useful when it comes to putting on the gloves as described further hereinafter. Preferably the abutment means is positioned to contact the hand between the thumb and index finger.

Conveniently the housing comprises a form of cage or hoop provided with said respective openings or alternatively may comprise a respective housing for each opening. Where a respective housing is provided for each opening it is convenient to form the housing from a tube-like structure, preferably of solid wall configuration but optionally having an open mesh construction. More preferably each housing has an aperture in a wall thereof through which a thumb of the glove may project. Preferably the thumb glove will overly part of said wall when projecting through said aperture. Said aperture conveniently provides the aforesaid abutment to limit penetration of the glove in to the housing. The tube-like structure may be formed as a moulding in the shape of an oversize fingered glove or mitten. It is preferable if fingers are open at the ends to aid cleaning. The thumb is open to assist removal as described further hereinafter.

Depending on the material of the gloves, different materials will impart sufficient exterior grip on the gloves. For relatively loose fitting industrial rubber gloves we have found that a polypropylene material in the form of a plastic pipe works quite well. A 100 mm diameter pipe will accommodate a large range of hand sizes.

In use an operator pushes each of his gloved hands into the respective opening and inserts the thumbs in to the thumbholes. An informal wedging action occurs with the glove of the thumb gripping the aperture and the contact of other external parts of the glove assist in holding the glove in the housing so that the operator can then withdraw his hands. Often the friction generated between the glove and the housing is sufficient to hold the gloves and allow the hands to be pulled free. In certain circumstances where the gloves are a tight fit additional resistance may have to be applied to the gloves and this can be achieved by positioning the respective housings such that it is possible for the gloved thumb of one hand to contact the gloved thumb of the other hand. By this means an operator can hold the gloved thumb of one hand in contact with the exterior of the housing with the thumb of the other hand to aid release of each hand from the glove.

The gloves can be left in the housings ready to put on when the operator next needs them.

Putting on the gloves simply requires the operator to push his hands into the gloves. The movement of the gloves away from the operator is limited by the aforesaid aperture/abutment means. Thus the gloves can be put on without having to contact the exterior of the gloves.

Figure 2:
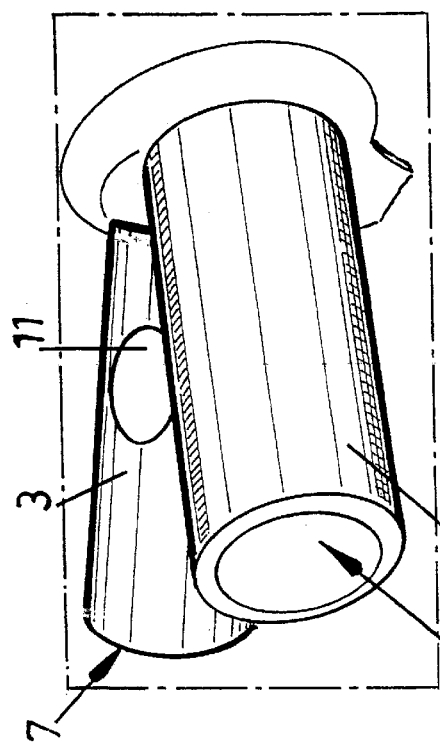
Figure 3:
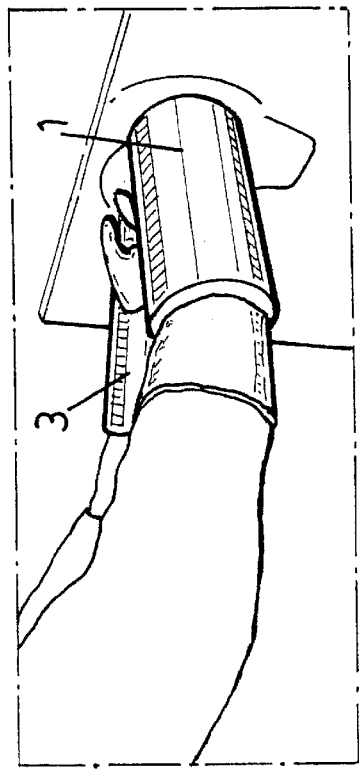
Figure 4:
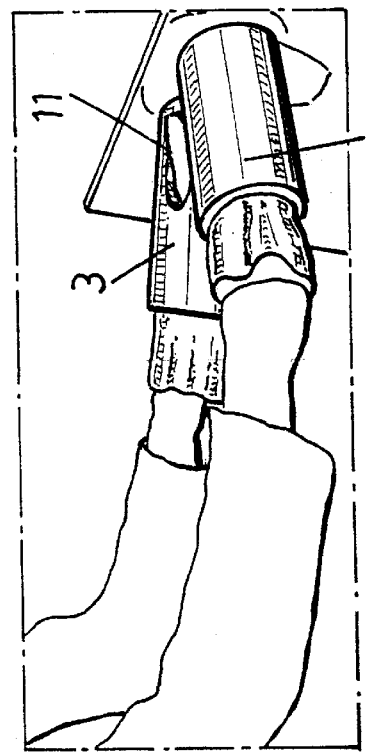

The present invention will now be described further by way of example only with reference to the accompanying drawings in which:

FIG. 1 is a perspective view from front and above of one embodiment of glove housing according to the invention, FIG. 2 is a perspective view from one side and above of the embodiment of FIG. 1, FIG. 3 is a perspective view of housings of FIG. 1 and 2 with gloved hands in position and FIG. 4 illustrates the housing with the gloves retained therein once the hands have been removed.

Referring to the drawings, one embodiment of apparatus embodying the invention is illustrated and comprises two tubular housings 1, 3 fixedly mounted with respect to any suitable supporting structure and having respective openings 5, 7 in one end thereof and respective apertures 9, 11 in the side walls thereof. As will be seen from the illustration the respective apertures are generally elliptical.

The apparatus provides a means for removing gloves from the hands of an operator without the operator having to contact the gloves with his bear hands and the apparatus also provides a means of holding the gloves whilst the operator's hands are removed therefrom.

When an operator wishes to remove the gloves from his hands he inserts his left and right gloved hands into a respective one of the two housings as shown in FIG. 3 and inserts his thumbs through the respective apertures 9, 11. The positioning of the housing is such that the gloved thumb of one hand can contact the gloved thumb of the other hand and hold it in contact with the outer surface of the housing and similarly for the other hand. As will be seen from the illustration the housings are aligned so that their respective axis converge towards one another from the end openings. The contact of the gloves with the respective housings applies a resistance thereto which will be apparent on any attempt to remove the hands from the gloves. If this resistance by itself is not sufficient to free the hands without the gloves releasing from the housing then further resistance can be added by the gloved thumb of one hand contacting the thumb glove of the other hand holding it in contact with the housing so that that hand can be pulled free or at least its release initiated. Before completely pulling one hand free an operator can urge the other thumb glove into contact with the housing to initiate release of that hand and then the hands can be removed from the gloves leaving the gloves in place in the housing.

When an operator wishes to put on the gloves he simply inserts his hands into the open ends of the gloves which are presented to him in the housings and into the respective fingers and thumbs. The presence of the gloved thumb projecting through the aperture serves to limit the movement of the gloves into the housing thereby enabling the operator to insert his fingers and thumbs fully into the fingers and thumbs of the respective gloves. The operator can then close together his fingers so as to imply a gripping force on the gloves enabling them to be withdrawn from the housings as the gripping force on the gloves is greater than the gripping force applied by the housing.

Other configurations of housings for the gloves can be envisaged other than the tabular housings illustrated. Any housings, loop or hoop into which the gloved hands can be inserted and which applies a friction force thereto which is greater than the resistance of the gloves on the hand will suffice.

What is claimed is:

1. A method of removing and putting on gloves which avoids skin contact with the exterior of the gloves, the method comprising the steps of:

providing a housing having an opening or respective openings for left and right gloved hands;

pushing each gloved hand into the housing opening therefor and making frictional engagement of the glove with the housing without stretching of the glove; and withdrawing the hands from the gloves.

2. A method as claimed in claim 1 and further comprising inserting a thumb of the gloves into a respective thumbhole therefor to aid frictional engagement of the glove with the housing.

3. A method as claimed in claim 2 and further comprising contacting the glove thumb of one hand with the gloved thumb of the other hand and partially withdrawing said one hand from the glove before contacting the glove thumb of the other hand with the gloved thumb of the one hand and withdrawing said other gloved thumb.

4. A method as claimed in claim 1 in which the gloves are retained in the housing after removal of the hands, and putting on the gloves comprises reversing the procedure.

5. Apparatus for use in removing and retaining gloves, comprising:

housing means having opening means to receive, in use, a respective left and right gloved hand, the housing means providing means which is dimensioned to be contactable with the exterior of each glove in a light gripping or frictional manner without stretching of the glove and wherein the contact force offers a resistance to removal of the glove on withdrawal of a band from the glove;

wherein the housing means has aperturing to receive a thumb of each glove to aid frictional engagement of the glove with the housing and to limit penetration of the glove into the housing; and in which the aperturing is formed in a wall of the housing means and, in use, the thumb of the glove overlies part of said wall when projecting through said aperture and in which the position of the aperturing is such that the left and right gloved thumbs can contact each other.

6. A method of removing and putting on gloves which avoids skin contact with the exterior of the gloves, the method comprising the steps of:

providing a housing having an opening or respective openings for left and right gloved hands;

pushing each gloved hand into the housing opening therefor and making frictional engagement of the glove with the housing without stretching of the gloves;

inserting a thumb of the gloves into a respective thumbhole therefor to aid frictional engagement of the glove with the housing and to limit penetration of the glove into the housing; and withdrawing the hands from the gloves.

7. A method as claimed in claim 1, further comprising contacting the glove thumb of one hand with the gloved thumb of the other hand and partially withdrawing said one hand from the glove before contacting the glove thumb of said other hand with the gloved thumb of said one hand and withdrawing said other gloved thumb.

8. A method as claimed in claim 6, in which the gloves are retained in the housing after removing the hands, and putting on the gloves comprises reversing the procedure.

* * * * *